(12) United States Patent
Bob

(10) Patent No.: US 11,666,376 B2
(45) Date of Patent: Jun. 6, 2023

(54) ELECTROSURGICAL INSTRUMENT

(71) Applicant: Erbe Elektromedizin GmbH, Tuebingen (DE)

(72) Inventor: Felix Bob, Rottenburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 405 days.

(21) Appl. No.: 16/881,392

(22) Filed: May 22, 2020

(65) Prior Publication Data

US 2020/0375654 A1 Dec. 3, 2020

(30) Foreign Application Priority Data

May 27, 2019 (EP) .................................... 19176740

(51) Int. Cl.
 *A61B 17/28* (2006.01)
 *A61B 18/14* (2006.01)
 (Continued)

(52) U.S. Cl.
 CPC ........ *A61B 18/1445* (2013.01); *A61B 17/285* (2013.01); *A61B 17/2816* (2013.01);
 (Continued)

(58) Field of Classification Search
 CPC ... A61B 17/28; A61B 17/2816; A61B 17/285; A61B 17/29; A61B 17/295;
 (Continued)

(56) References Cited

U.S. PATENT DOCUMENTS 7,131,970 B2 * 11/2006 Moses ................ A61B 18/1442
 606/205
8,357,159 B2 1/2013 Romero
 (Continued)

FOREIGN PATENT DOCUMENTS

AU 2014205809 B2 8/2015
EP 1532932 A1 5/2005
 (Continued)

OTHER PUBLICATIONS

European Extended Search Report dated Dec. 5, 2019, in corresponding European Application No. 19176740.9, with machine English translation (12 pages).

*Primary Examiner* — Michael F Peffley
(74) *Attorney, Agent, or Firm* — Fitch, Even, Tabin & Flannery LLP

(57) ABSTRACT

An electrosurgical instrument with first and second branches pivotably arranged at a hinge is disclosed. The hinge is formed by a support pin at the second branch and a corresponding support cavity at the first branch. At one side adjacent to the hinge location at which the support pin extends into the support cavity, a knife guide cavity is provided in the second branch for a moveable guided support of a knife. Parallel to the pivot axis defined by the hinge, the knife guide cavity is arranged adjacent to an axial end of the support pin. The hinge or the hinge location formed by the hinge at which the support pin is arranged in the support cavity is only arranged on one side of the knife guide cavity viewed in a direction parallel to the pivot axis. The respective other side is free from hinge components.

15 Claims, 7 Drawing Sheets

(51) Int. Cl.
*A61B 17/285* (2006.01)
*A61B 17/29* (2006.01)
*A61B 18/12* (2006.01)

(52) U.S. Cl.
CPC . *A61B 2017/2947* (2013.01); *A61B 2018/126* (2013.01); *A61B 2018/1455* (2013.01)

(58) Field of Classification Search
CPC .... A61B 2017/2947; A61B 2017/2939; A61B 18/1445; A61B 18/1442; A61B 2018/126; A61B 2018/1455; A61B 2090/0813
See application file for complete search history.

(56) References Cited

U.S. PATENT DOCUMENTS

| | | | |
|---|---|---|---|
| 8,574,230 B2 | 11/2013 | Romero | |
| 9,005,200 B2* | 4/2015 | Roy | A61B 18/1442 606/205 |
| 9,221,184 B1* | 12/2015 | Wada | A01G 3/021 |
| 9,345,534 B2* | 5/2016 | Artale | A61B 18/1442 |
| 9,498,280 B2 | 11/2016 | Garrison | |
| 2003/0199869 A1 | 10/2003 | Johnson et al. | |
| 2018/0325580 A1* | 11/2018 | Sims | A61B 18/1233 |

FOREIGN PATENT DOCUMENTS

| | | |
|---|---|---|
| EP | 1372512 B1 | 6/2005 |
| EP | 1609430 B1 | 8/2011 |
| EP | 2436328 A1 | 4/2012 |
| EP | 2040634 B1 | 6/2014 |
| EP | 2112909 B1 | 3/2015 |
| EP | 2926748 A1 | 10/2015 |
| EP | 2286752 B2 | 5/2016 |
| WO | 02/080798 A1 | 10/2002 |
| WO | 2013/134044 A1 | 9/2013 |
| WO | 2017/031506 A1 | 2/2017 |

* cited by examiner

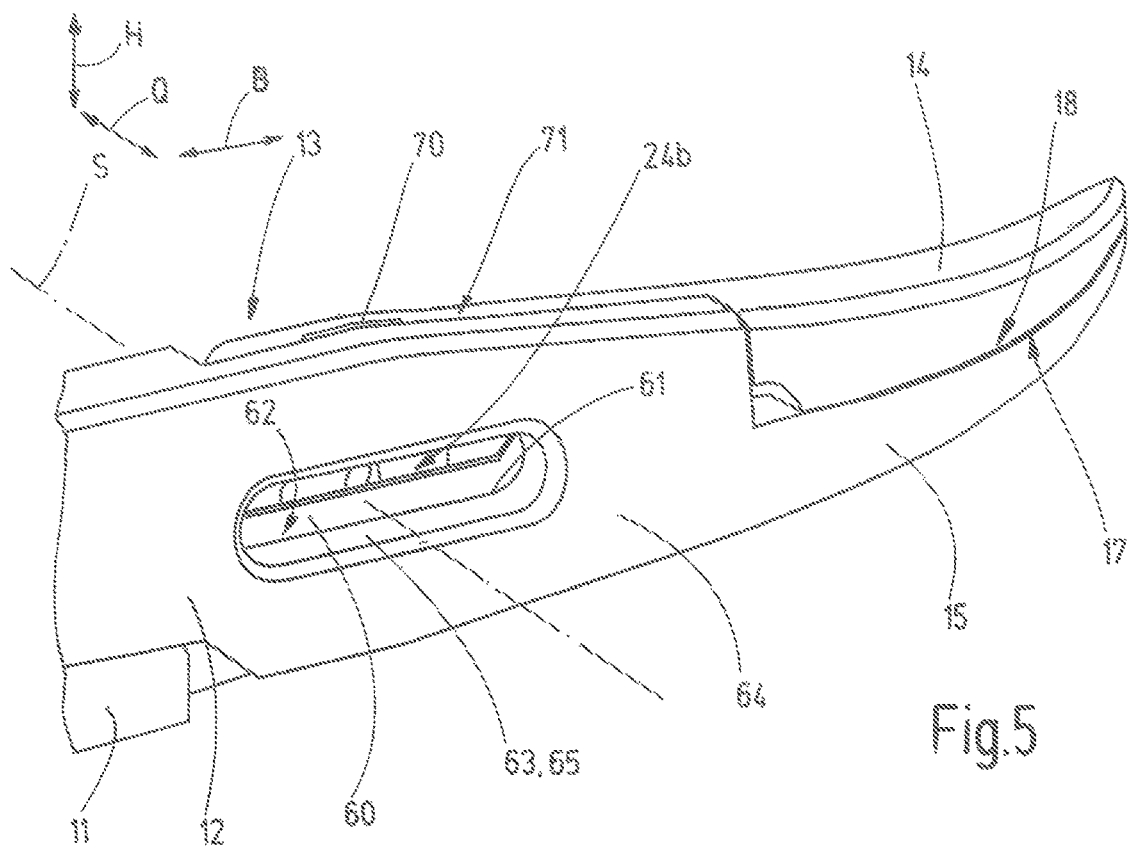
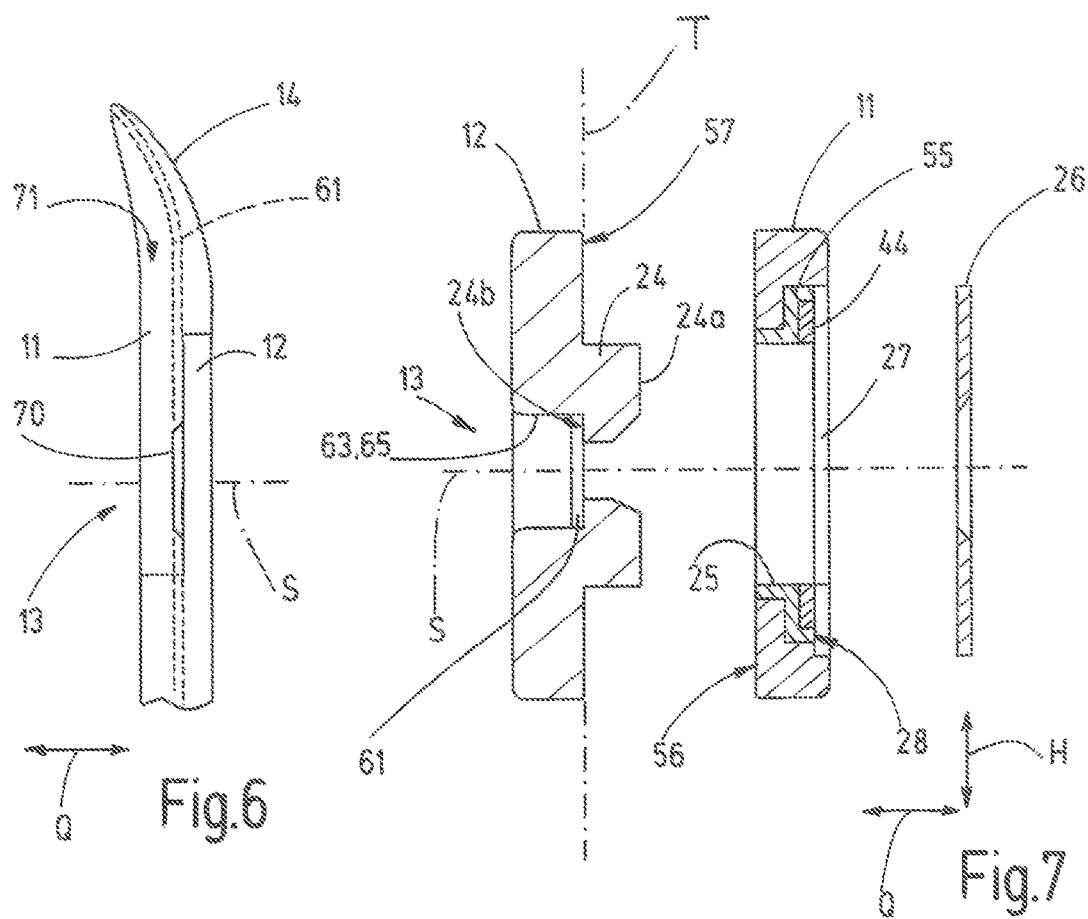

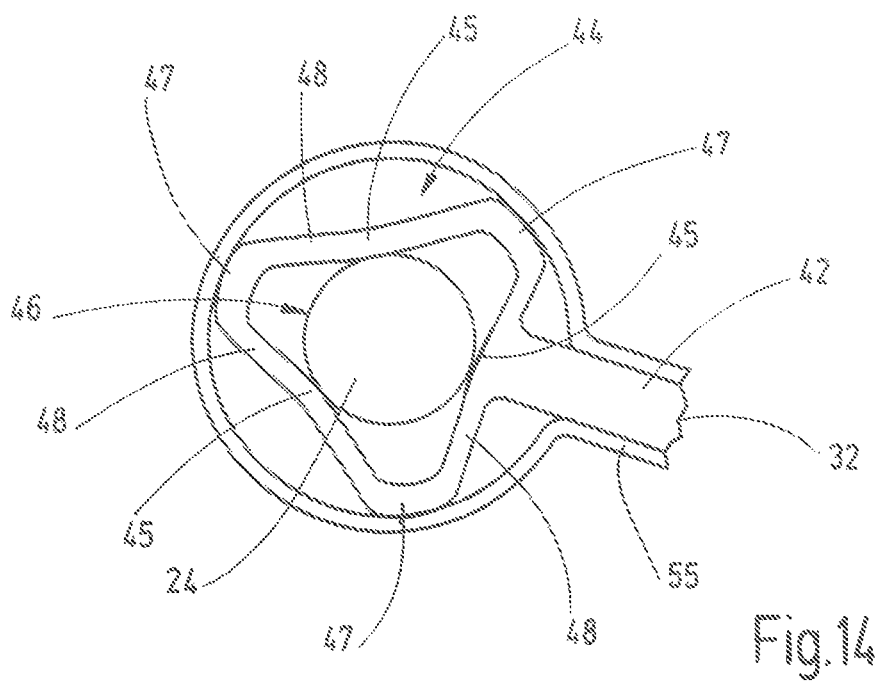
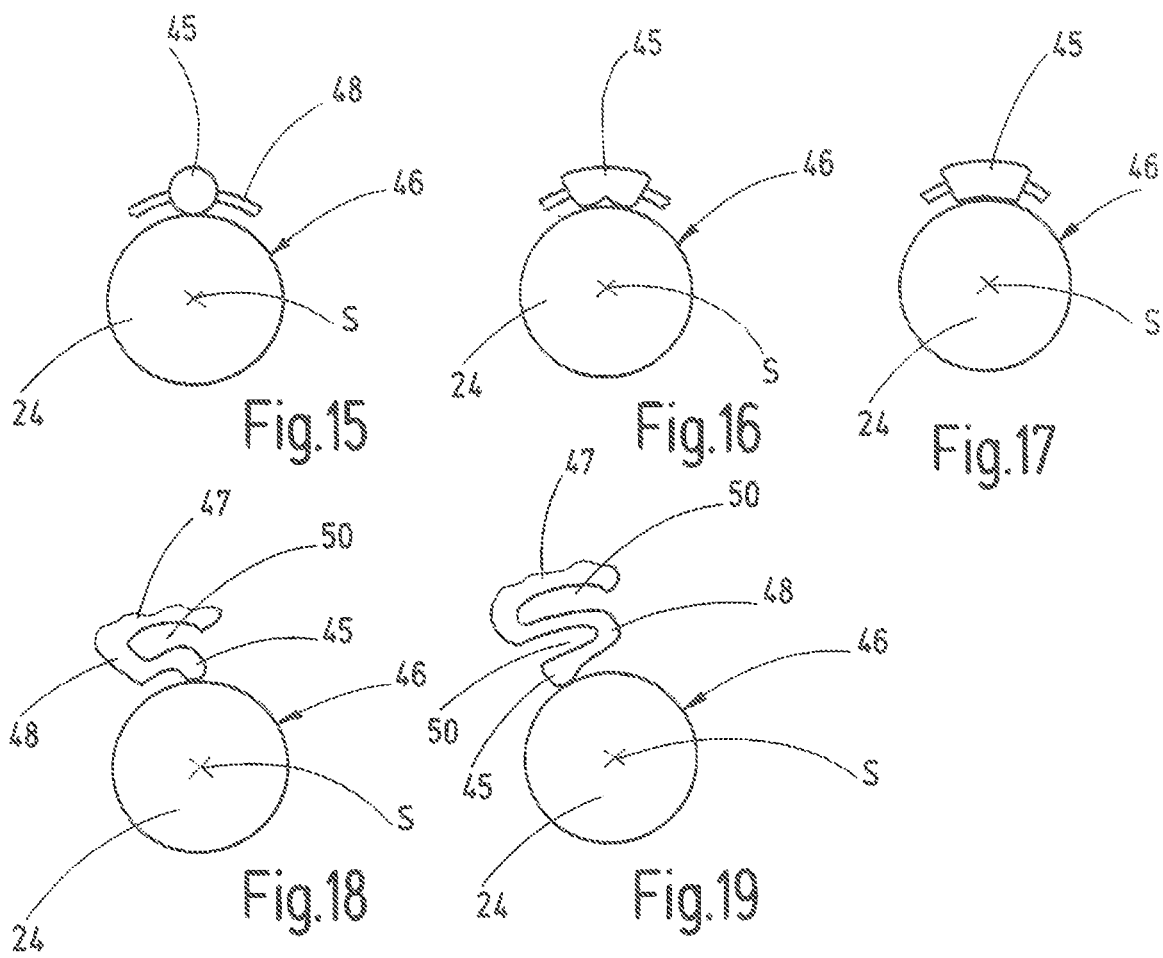

ELECTROSURGICAL INSTRUMENT

RELATED APPLICATION(S)

This application claims the benefit of European Patent Application No. 19176740.9, filed May 27, 2019, the contents of which are incorporated herein by reference as if fully rewritten herein.

TECHNICAL FIELD

The invention refers to an electrosurgical instrument that can be used, e.g. for thermofusion or coagulation, as well as a method for manufacturing the electrosurgical instrument. The electrosurgical instrument has two branches, each having a jaw part, wherein each jaw part comprises a tissue contact surface. Via the tissue contact surfaces a current can be conducted through biological tissue clamped in between, e.g. in order to seal the tissue.

BACKGROUND

An electrosurgical instrument with two branches supported at each other in a hinged manner and a knife that is moveably supported in a knife guide cavity is known from EP 2926748 A1. The two branches are configured in U-shape in the hinge area. Thus, each branch has two side walls that extend parallel and with distance to each other. In each branch at one side wall a support cavity and at the respective other side wall a hollow cylindrical support pin is provided that extends toward the outside. The two branches can be connected via two hinges wherein the support pin of one branch engages in the support cavity of the respective other branch. In doing so a free space is created between the two hinges in which a first guide component and a second guide component can be inserted to form a knife guide cavity. The two guide components are connected with each other by means of a latched connection for forming the knife guide cavity. At one guide component a flexible web is formed that engages in one of the two hollow cylindrical support pins of one hinge. Due to this engagement and due to the arranging the guide components between the hinges also the two branches are locked against an unintended release of the hinge connection.

U.S. Pat. No. 8,574,230 B2 describes an electrosurgical instrument with two branches that are supported at each other in a hinged manner by means of a hinge. The hinge has a hinge body that is torque-proof connected with one of the two branches. At the hinge body the support pins are present on opposite sides in order to allow a hinged support of the branches. The branch that is pivotably arranged relative to the hinge body comprises a knife and a knife actuation and is configured from multiple parts. In order to guide the knife through the hinge, the hinge body has a slit that extends between its two support pins orthogonal to the pivot axis. The slit is aligned with the adjacent knife guide cavity only if the branches are closed. In the open position of the branches the slit of the hinge body is pivoted from the extension direction of the adjacent knife guide and thus impedes a knife actuation. A similar device is also described in U.S. Pat. No. 8,357,159 B2 and EP 2 112 909 B1.

An instrument for sealing a vessel and for separating large tissue structures is known from EP 2 286 752 B2. Two branches are pivotably supported at each other by means of a pivot pin. In alignment with a knife guide cavity a slot hole passes through the pivot pin in order to allow the knife to pass through along the knife guide.

In the instrument described in EP 2 040 634 B1 a support pin for pivotably supporting two branches is provided with a through hole for passing a knife therethrough.

The instrument described in EP 1 609 430 B1 has an eccentric knife guide with distance to a pivot axis defined by a hinge by means of which two branches are supported in a hinged manner at each other. Thus, the knife is eccentrically arranged relative to the pivot axis. An eccentric support of the knife is undesired.

U.S. Pat. No. 9,498,280 B2 discloses an instrument in which two branches are supported at each other in a hinged manner by means of a hinge pin. The hinge pin has a through opening through which a knife actuation is passed.

Another instrument in which a knife is guided through a pivot pin is described in U.S. Pat. No. 9,498,280 B2. Other configurations of electrosurgical instruments are known from EP 1 372 512 B1 and AU 2014 205 809 B2.

Starting from the prior art it can be considered as an object of the present invention to provide an instrument in which a simple configuration of the knife guide on the level of the pivot axis is allowed.

SUMMARY

According to the invention the electrosurgical instrument has a first branch that comprises a support cavity and a second branch that comprises a support pin. The support pin engages the support cavity. In doing so, a hinge is formed by means of which the first branch is pivotably supported about a pivot axis at a second branch. The pivot axis is defined by the support pin and/or the support cavity. A transverse direction is orientated parallel to the pivot axis.

In the second branch a knife guide cavity is provided in which a knife is moveably supported in a guided manner in a movement direction. The knife guide cavity extends in movement direction passing by the pivot axis or the support pin to and into the second jaw in the distal end area of the electrosurgical instrument. The knife guide cavity extends on the level of the support pin and the support cavity. Preferably, the pivot axis extends through the knife guide cavity. The knife guide cavity and the knife arranged therein are thus non-eccentrically arranged relative to the pivot axis or the hinge.

In the transverse direction the support pin is arranged adjacent to the knife guide cavity on the one side, whereas the second branch is free of any support pin or any support cavity on the other side. Thus, the second branch has no hinge parts on this other side. Thus, the hinge is formed only on the one side relative to the knife guide cavity, whereas the respective other side is configured without hinge or hinge location. The knife guide cavity passes by the hinge. The knife guide cavity does not extend through hinge components of the hinge.

At least in the area of the hinge and from there to the distal end of the second branch, the knife guide cavity is arranged at an inner position and can be limited in at least one section by the first branch—at least in the closed position of the branches. Thus, the knife guide cavity is not positioned in this area at the outer side of the second branch facing away from the first branch.

Due to this configuration, the knife can be arranged in movement direction on the level of the pivot axis or the hinge. An eccentric support of the knife is avoided. The pivot axis can extend through the knife guide cavity. However, a very simple configuration of the hinge is ensured. Hinge configurations in which the knife must be passed through the support pin are not necessary. Also providing two separate hinges along a common pivot axis can be avoided.

Thus, a very simple manufacturing and a good accessibility of the hinge and of the knife guide cavity are ensured in order to be able to clean the electrosurgical instrument after use.

Preferably only one single support pin and one single support cavity is present that form one single hinge and thus one single support location.

In an embodiment the first branch comprises a first abutment surface into which the support cavity opens. The second branch can comprise a second abutment surface from which the support pin extends. The two abutment surfaces face each other and preferably directly or indirectly abut against each other.

It is also advantageous, if the first abutment surface and/or the second abutment surface forms a separation plane. The two branches are particularly only hinged at each other via the one hinge. The hinge is present on one side of the separation plane in transverse direction. The separation plane preferably extends in a plane. The separation plane is preferably orientated orthogonal to the pivot axis. The knife guide cavity can be arranged adjacent to the separation plane and can particularly directly adjoin the separation plane.

It is advantageous, if the knife guide cavity is open toward the second abutment surface. In doing so, the cleaning of the knife guide cavity or the knife after use of the instrument is simplified. Preferably, the knife guide cavity is open toward the second abutment surface on both sides of the pivot axis or the support pin with view in movement direction of the knife.

In a preferred embodiment a transverse cavity extending in transverse direction can be provided in the second branch. The transverse cavity opens at one end in the knife guide cavity and at its opposite other end in transverse direction in an outer side of the second branch. The outer side of the second branch is preferably facing away from the first branch. The pivot axis extends preferably through the transverse cavity. In an embodiment the transverse cavity can be configured as slot hole. The slot hole can have a length in movement direction of the knife that is at least as long as the diameter of the support pin.

By means of the transverse cavity the accessibility of the knife guide cavity in the area of the support pin is improved, e.g. for cleaning purposes.

The support pin can adjoin a knife guide cavity directly with an axial end face. Particularly the support pin has no through opening that is suitable for passing a knife and that extends through the support pin between its two axial end faces. The support pin limits the knife guide cavity particularly at most at three sides.

In a preferred embodiment a purge opening is provided in the first branch. The purge opening opens at one end in the support cavity and at the opposite other end in an outer side of the first branch. The purge opening extends between its two ends in an extension direction substantially orthogonal to the pivot axis. The purge opening is preferably open on a side facing the second branch. In one embodiment the purge opening opens in a narrow side of the first branch.

The purge opening is arranged between its two ports along a section of the knife guide cavity in a predefined opened position of the branches. In this opened position the purge opening extends particularly completely along the section of the knife guide cavity. Through the purge opening the access of the knife guide cavity is further improved and the cleaning of the instrument is simplified. The predefined open position is, for example, the completely opened position of the branches with the maximum opening angle between the two jaws of the branches.

Another aspect of the electrosurgical instrument refers to the electrical connection of, and the supply of current to, the tissue contact surfaces at each jaw of the branches. This design of the electrosurgical instrument can be used independent of the previously described features concerning the guidance of a knife in a knife guide cavity.

The electrosurgical instrument according to this further aspect has a first branch and a second branch. At the second branch a support pin is arranged defining a pivot axis. The first branch is pivotably supported on this support pin. Each branch has a jaw in the distal area with view from the pivot axis and a handling part with view from the pivot axis to the proximal end of the electrosurgical instrument. An electric connection device for an external cable is, for example, arranged at the first branch or at one single other location. The connection device is electrically connected via a first conductor with a first tissue contact surface of the first branch and via a second conductor with a second tissue contact surface of the second branch. The two electric conductors and the two tissue contact surfaces are electrically insulated from each other such that different electrical potentials can be applied to the two tissue contact surfaces.

For example, each branch can have an electrically conductive core that is at least partly enclosed with an electrically insulating plastic material. The electrically insulating plastic material can form an electrically insulating outer layer and can be applied on the core by an injection molding process for example.

The second conductor is integrally formed and has a contact section with at least one contact part at its distal end. The at least one contact part abuts at an outer surface of an electrically conductive area of the support pin, e.g. at a radially outward orientated circumferential surface or at an axially orientated ring surface. Particularly, the at least one contact part is biased radially against the circumferential surface of the support pin. In doing so, an electrically conductive rotation joint between the support pin and the at least one contact part is established. In this manner an electric connection between the second conductor in the first branch and the second tissue contact surface in the second branch can be established. The support pin thus forms a part of the electric connection between the second conductor and the second tissue contact surface. In the second branch the support pin can be connected with the second tissue contact surface, e.g. via a conductive core of the second branch. The connection between the support pin and the second tissue contact surface in the second branch can also be realized by means of a further electric conductor or in another manner.

The radial sliding contact connection between the at least one contact part and the support pin forms a reliable electrical connection and can be very easily established. The second conductor including the contact section can be produced very easily by separating the second conductor with the contact section and with the at least one contact part of a plate, e.g. by punching, by separation with use of a laser, by water jet cutting or by an etching process. The second conductor does not need to be further worked after separation from the plate, however, it can also be worked as an option. Preferably, the second conductor extends inside the first branch completely along or inside a first extension plane.

At least in sections the two conductors can have the form or shape of a strip conductor. Analog to the second conductor the first conductor can be configured integrally. It can also extend completely along or in an extension plane.

It is advantageous, if the first conductor and the second conductor are arranged in a common opening in the first branch. As an alternative the two conductors could also be arranged in respective openings separated from each other. For example, the two conductors can be placed in a form together with an electrically conductive core for manufacturing of the second branch and can be overmolded with plastic or can be insertions molded in plastic, e.g. by an injection molding process.

It is preferred, if an electrically insulating intermediate layer is arranged between the first conductor and the second conductor. The intermediate layer is positioned in a sandwich-like manner between the two conductors. The electrically insulating intermediate layer can be created on the first conductor and/or the second conductor, e.g. by form fitting or overmolding, before the two conductors are subsequently connected with each other for forming the second branch.

It is further advantageous, if an electrically insulating intermediate layer is arranged between the second conductor and an electrically conductive core of the first branch. This intermediate layer can also concurrently form the electrically insulating intermediate layer between the second conductor and the first conductor.

It is preferred, if the electrically insulating intermediate layer is fixedly applied on the second conductor, e.g. by an injection molding process. The electrically insulating intermediate layer can also be joined with the second conductor by gluing or another method. The joint between the second conductor, the intermediate layer applied thereon and the first conductor is preferably only established during manufacturing of the first branch.

In an embodiment the second conductor has a conductor section with a rectangular cross-section that adjoins the contact section. In a preferred embodiment the cross-section is constant with regard to its size and/or shape.

It is also advantageous, if the second conductor comprises a connection section adjoining the conductor section, the connection section being electrically connected with the connection device or forming a part of the connection device. In one embodiment the connection section can be a plate-shaped extension of the conductor section.

Preferably the first conductor and/or the second conductor has a rectangular cross-section at each location along its extension.

In one embodiment the contact section completely surrounds the support pin in a circumferential direction about the pivot axis. In another embodiment the contact section may surround the support pin only partly in circumferential direction, e.g. about at least 50% or at least 60% or at least 70% of the circumference.

In a preferred embodiment at least one holding part is formed at the contact section that is elastically biased toward the support pin, wherein at each holding part a contact part or multiple contact parts or all of the contact parts are arranged. Due to the holding part being integrally formed with the second conductor, additional biasing means can be omitted in order to bias the contact part against the circumferential surface of the support pin.

In addition, the contact section can comprise at least one support part. By means of the support part the contact section can be supported at a radially outer side at the first branch, the radially outer side being arranged with distance opposite the support pin. For example, the support part can be supported at the electrically conductive core of the second branch via an electrically insulating intermediate layer.

It is advantageous, if a through hole is present between the at least one support part and the at least one contact part that completely extends through the contact section. In doing so, a clearance is created between the support part and the contact part in order to spring elastically bias the contact part against the support pin. The through hole can be surrounded by the support part and/or the holding part of the contact section or can be open at one location.

In an embodiment the support pin has a cylindrical circumferential surface. At least the electrically conductive area of the support pin is formed by a cylinder skin surface. In another embodiment the support pin or the electrically conductive area of the support pin can be formed by the skin surface of a truncated cone. Thus, the support pin can have at least one conical section or can be completely conically configured.

If the support pin comprises at least one conical section, a pressing part can be provided that creates an axial force parallel to the pivot axis on the at least one contact part. Due to the electrically conductive surface of the support pin arranged obliquely to the pivot axis, also a radially pressing force between the at least one contact part and the support pin is created thereby.

The electrosurgical instrument described above can be manufactured by taking the following steps:

separating a first conductor from a plate and separating a second conductor from a plate;

electrically connecting the first conductor with a first tissue contact surface;

arranging of the first tissue contact surface, the first conductor and the second conductor in a first die and creating a first branch by inserting of a pourable, curable material in the first die, such that the at least one contact part of a contact section of the second conductor is arranged in a support cavity of the first branch;

arranging of an electrically conductive support pin and a second tissue contact surface electrically connected with the support pin in a second die and creating a second branch by inserting a pourable, curable material in the second die; and inserting the support pin of the second branch in the support cavity of the first branch for establishing the hinged joint of the two branches at each other.

In all of the embodiments of the electrosurgical instruments that have been explained above, the instrument can be configured as single use instrument or reusable instrument.

BRIEF DESCRIPTION OF THE DRAWINGS

Preferred embodiments of the invention yield from the dependent claims, the description and the drawings. In the following preferred embodiments of the invention are explained in detail based on the attached drawings. The drawings comprise the following:

FIG. 5 shows a distal end section of an electrosurgical instrument in a perspective partial illustration, FIG. 6 shows a schematic top view of a distal end section of an electrosurgical instrument, FIG. 7 shows a cross-section illustration through a hinge of two branches of the electrosurgical instrument pivotably supported at each other, wherein the branches are shown in exploded view, FIG. 14 shows a schematic illustration of another embodiment of the contact section of the second conductor, FIGS. 15-19 each show a schematic basic illustration of a configuration of a contact part of the contact section of the second conductor, FIGS. 20-23 each show a schematic cross-section view through an embodiment of the electrosurgical instrument with different configurations of the electric connection between the contact section of the second conductor in the first branch and the support pin in the second branch.

DETAILED DESCRIPTION

Each of FIGS. 1-4 shows an embodiment of an electrosurgical instrument 10 that is configures as bipolar instrument according to the example. The electrosurgical instrument has a first branch 11 and a second branch 12 that are pivotably arranged about a pivot axis S at each other by means of a hinge 13. The pivot axis S extends in a transverse direction Q.

Figure 1:
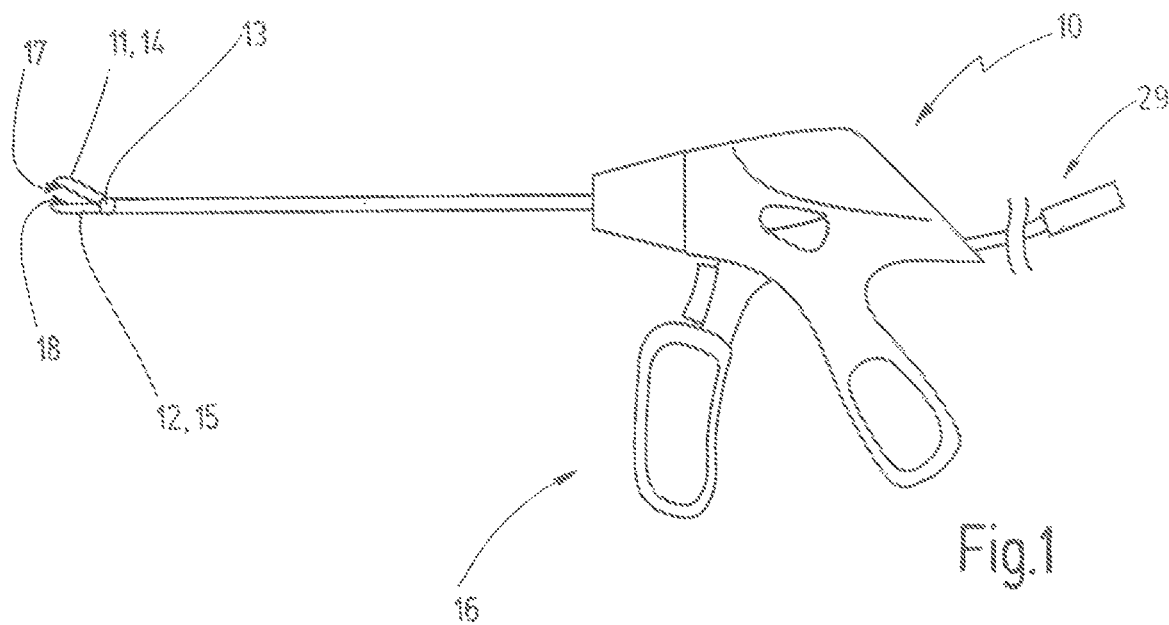
FIG. 1 shows a schematic side view of an embodiment of an electrosurgical instrument.

In the embodiment illustrated in FIG. 1 from the branches 11, 12 the jaws 14, 15 are substantially shown that extend originating from the pivot axis S or the hinge 13 in a distal area. The first jaw 14 and/or the second jaw 15 can be pivotably supported. For opening or closing the jaws 14, 15 the instrument 10 comprises a respective handling unit 16. By means of the handling unit 16 also further actions can be carried out, e.g. the application of voltage between a first tissue contact surface 17 at the first jaw 14 and a second tissue contact surface 18 at the second jaw 15 or the initiating of a current flow through tissue clamped or held between the tissue contact surfaces 17, 18. Additionally or alternatively, also a knife can be moved in a knife guide cavity along the jaws 14, 15 to the distal end, e.g. to separate tissue clamped or held between the jaws 14, 15. The knife and the knife guidance will be explained in greater detail later.

Figure 2:
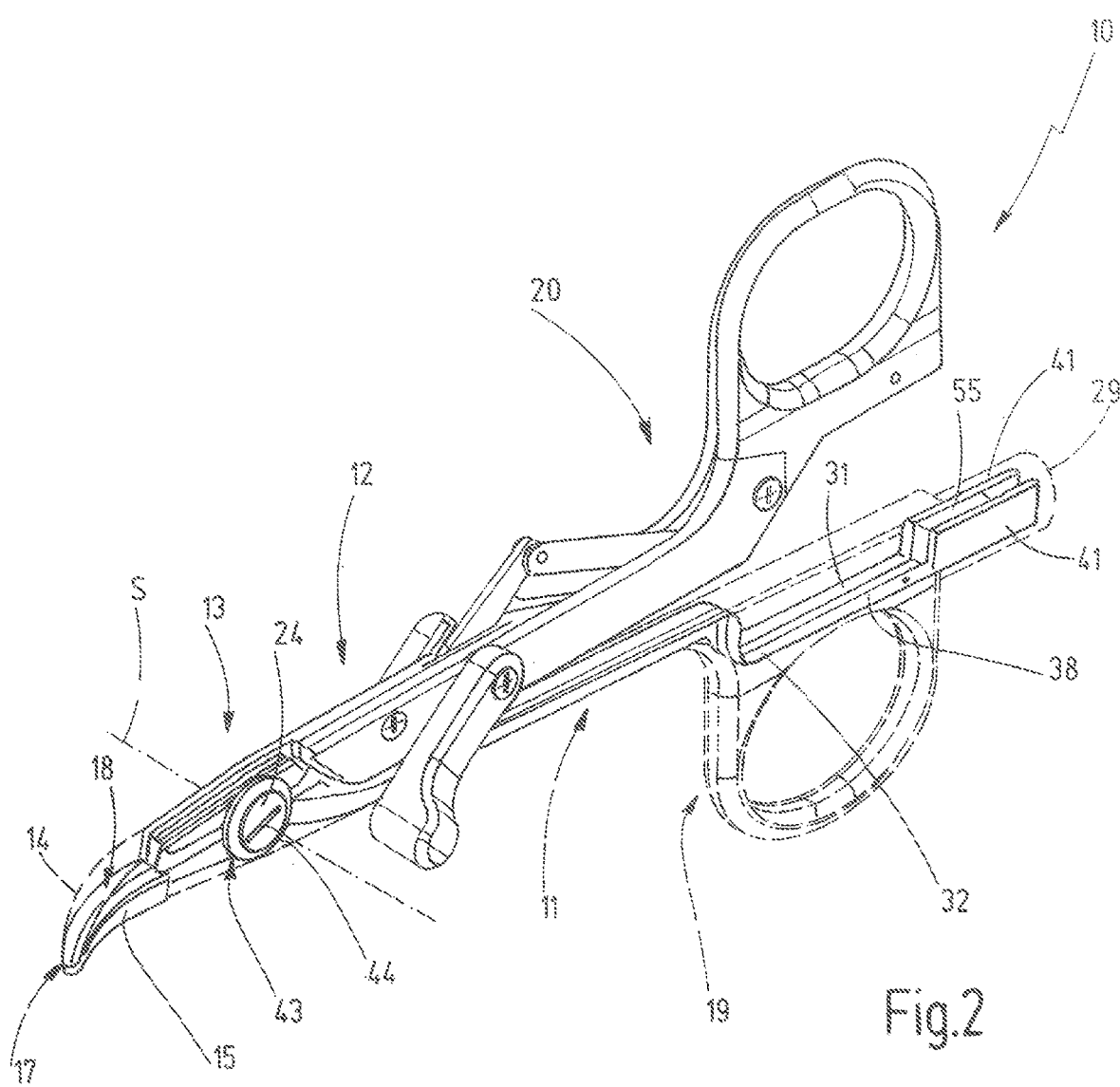
FIG. 2 shows a perspective illustration of another embodiment of an electrosurgical instrument.
Figure 3:
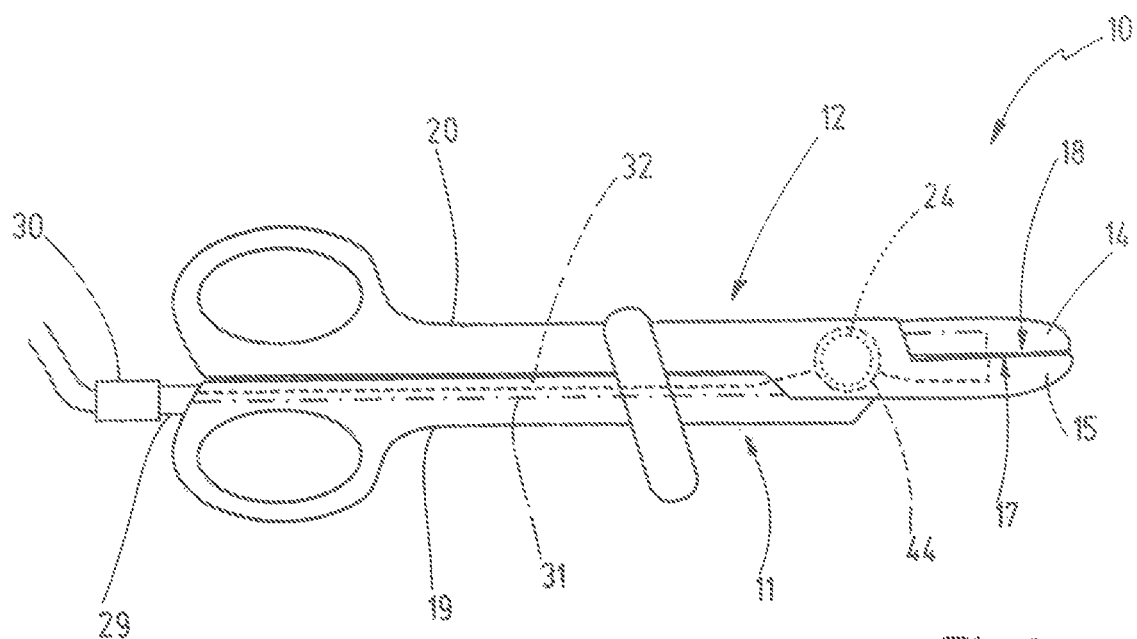
FIG. 3 shows a side view of an embodiment of an electrosurgical instrument as well as the electric connection in a block diagram-like illustration.
Figure 4:
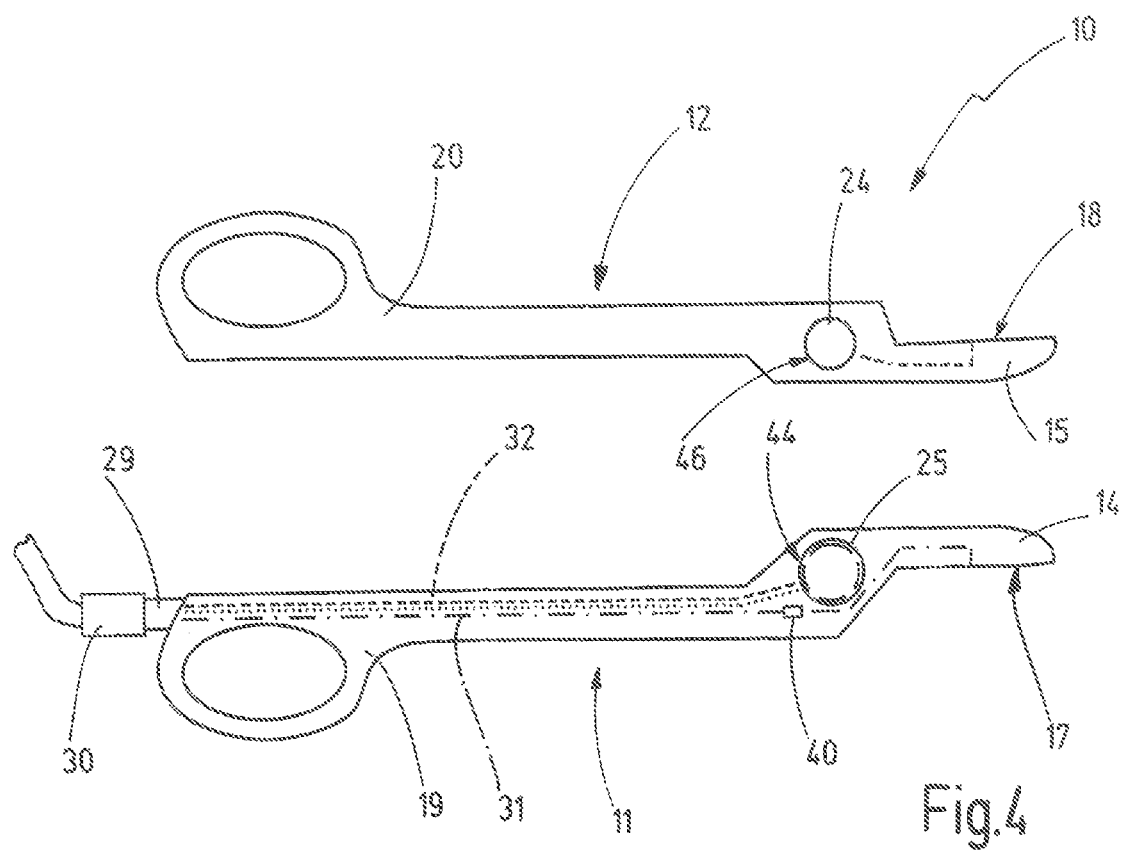
FIG. 4 shows a schematic side view of the first branch and the second branch of the electrosurgical instrument of FIG. 3.

Additional embodiments of an electrosurgical instrument are illustrated in FIGS. 2-4 that are configured in a scissors-like manner respectively. As apparent in the figures, the first branch 11 has a first jaw 14 originating from the pivot axis S in direction to the distal end and a first handling part 19 originating from the pivot axis S in direction to the proximal end. In accordance thereto a second branch 12 has a second jaw 15 originating from the pivot axis S in direction toward the distal end and a second handling part 20 originating from the pivot axis S in direction to the proximal end.

For forming the hinge 13 a support pin 24 defining the pivot axis S is present at the second branch 12, the support pin 24 engaging in a support cavity 25 formed at the first branch 11. The outer diameter of the support pin 24 corresponds—apart from a technically necessary play—to the inner diameter of the support cavity 25. The support pin 24 extends into the support cavity 25 and thus forms the hinge 13. As for example schematically illustrated in FIGS. 7-9, the joint between the support pin 24 and the support cavity 25 can be secured by means of a locking part 26 that can be connected with the free end 24a of the support pin 24. The locking part 26 can have a plate-shaped form and preferably has a circular outer contour.

Figure 8:
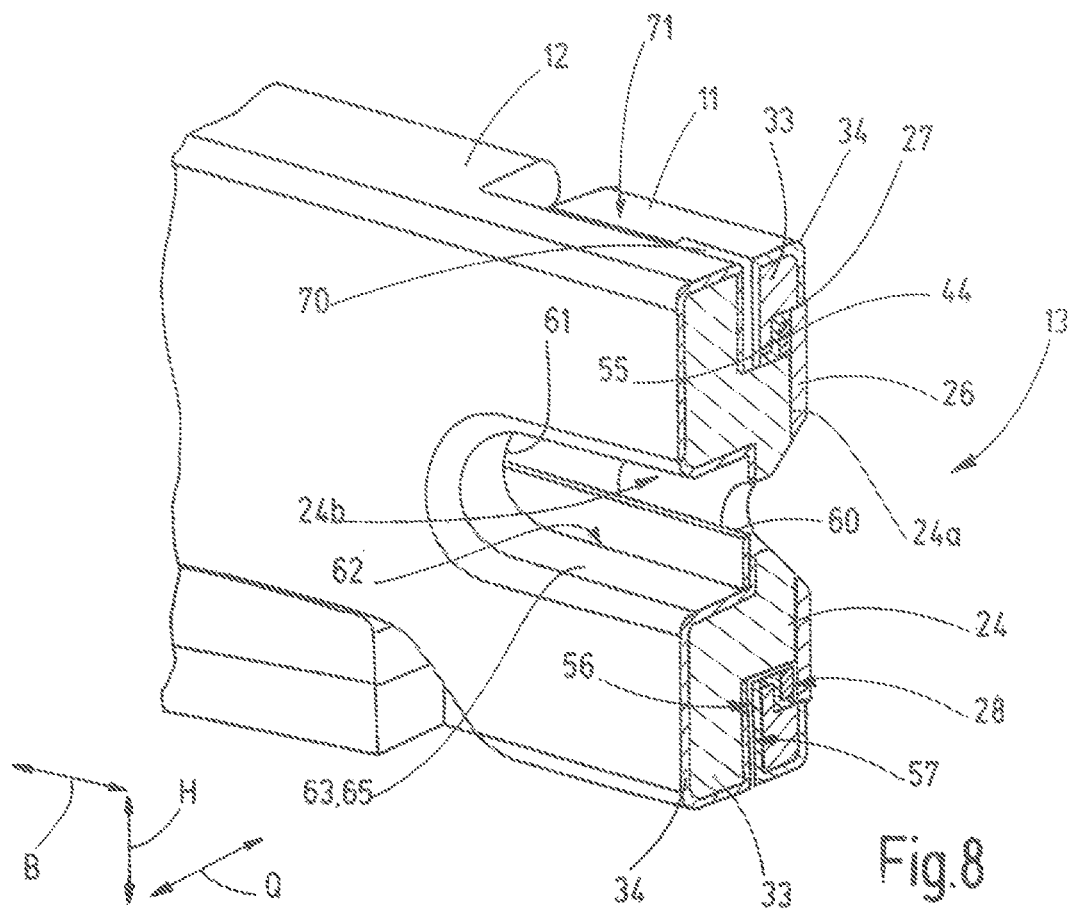
FIG. 8 shows a cross-section through the distal end section of the electrosurgical instrument of FIG. 5 along the pivot axis in a perspective partial illustration.

As particularly illustrated in FIGS. 7 and 8, the locking part 26 is positioned in a depression 27 provided at the first branch 11 in case the connection is established, wherein the depression 27 expands the support cavity 25 on the side of the second branch 12 facing away from the first branch 11, such that in so doing a ring shoulder 28 is created in the transition from the support cavity 25 to the depression 27. If the connection is established, the locking part 26 abuts at the ring shoulder 28. The locking part 26 is slidingly movably supported in the depression 27 relative to the first branch 11 according to the example and is torque-proof connected with the second branch 12 and according to the example with the support pin 24.

For establishing the electric connection the instrument 10 comprises a connection device 29 that is configured to be connected with an external electric connection 30 (FIGS. 3 and 4). The electric connection can be established by plugging the connection device 29 to the external electric connection 30 for example. If necessary, mechanical locking means can be present in order to avoid an unintentional disconnection of the electrical connection.

In the embodiments of the electrosurgical instrument 10 illustrated in FIGS. 2-4 the electric connection device 29 is provided at one of the branches and according to the example at the first branch 11. The electric connection device 29 is located at the proximal end of the first handling part 19. The electric connection device 29 is configured at least with two poles, wherein one pole is electrically connected by means of a first conductor 31 with the first tissue contact surface 17 and the second pole is electrically connected by means of a second conductor 32 with the second tissue contact surface 18. The electric connections are particularly illustrated in FIGS. 3 and 4. The first conductor 31 forms at least a part of the electric connection between the electric connection device 29 and the first tissue contact surface 17. It can indeed extend originating from the connection device 29 to the first tissue contact surface 17, however, also other electrically conductive components of the first branch 11 can be used to establish a part of the electric connection, particularly in the first jaw 14 of the first branch 11.

The second conductor 32 extends originating from the connection device 29 to the hinge 13. By means of the hinge 13 an electric connection between the second conductor 32 and the second branch 12 is established. The further electric connection between hinge 13 and the second tissue contact surface 18 is established in the second jaw 15 of the second branch 12.

As highly schematically illustrated in the perspective cut view of FIG. 8, the first branch 11 and the second branch 12 can have at least in the first jaw 14 and the second jaw 15 an electrically conductive core 33 that is at least partly enclosed by an electrically insulating outer layer 34. The outer layer 34 is provided in the area of the respective branches 11, 12 in which no electric connection shall be established to the outside. Preferably the outer layer 34 is provided everywhere outside the hinge 13 and outside of the respective tissue contact surfaces 17, 18. In doing so, a contact protection is created and a short circuit between the electrically conductive parts of the branches 11, 12 and particularly between the respective electrically conductive cores 33 is avoided.

Figure 10:
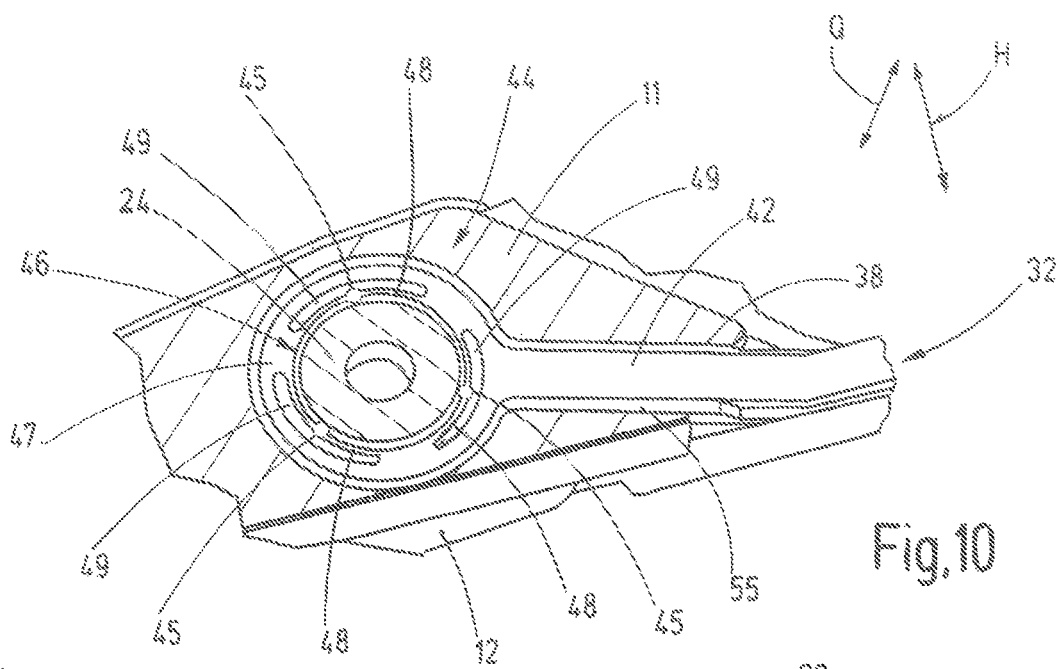
FIG. 10 shows a perspective partial view in a section orthogonal to the pivot axis with view on a contact section of an electric second conductor that is arranged in the first branch.
Figure 11:
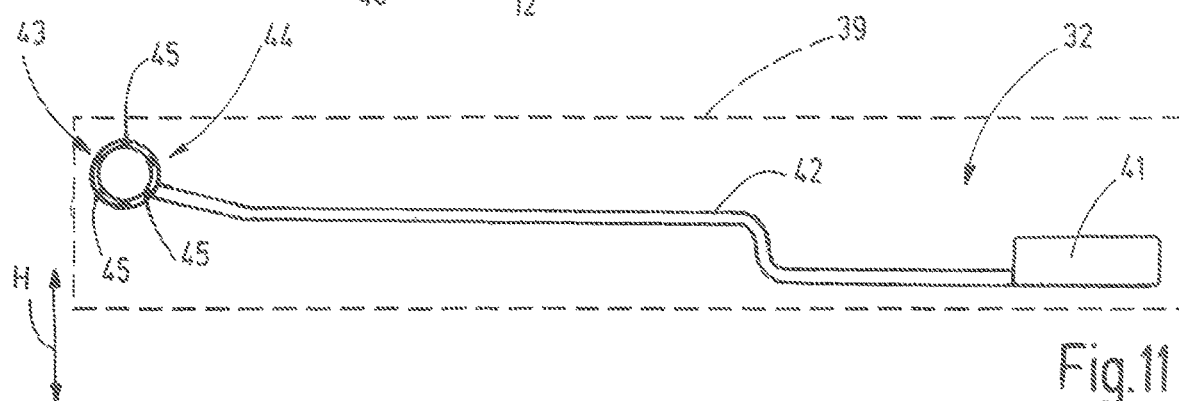
FIG. 11 shows a side view of the second electric conductor of FIG. 10, FIGS. 12 and 13 each show a basic sketch for illustrating the electric connection between the contact section of the second conductor and an electrically conductive circumferential area of the support pin.

As illustrated in FIGS. 2-4, the two conductors 31, 32 are arranged in the first branch 11. They can be arranged in a common opening 38 in the first branch 11 (FIGS. 2 and 10). In the embodiment the two conductors 31, 32 are each formed by one integral part. Each conductor 31 extends along an individual or a common extension plane that is orientated orthogonal to the pivot axis S. The conductors 31, 32 can be created by separation from a plate 39, as schematically illustrated in FIG. 11 for the second conductor 32. The separation can be carried out by punching, laser beam cutting, water jet cutting, etching or a combination of the mentioned procedures or any other separation method.

The first conductor 31 and the second conductor 32 are arranged adjacent to each other in transverse direction Q and can extend in an aligned manner at least in sections. As illustrated in FIG. 2, the conductors 31, 32 extend through the first handling part 19 predominantly in an aligned manner, according to the example at least from the connection device along an area of the first handling part 19, in which the first handling part 19 and the second handling part 20 are arranged adjacent to each other in a height direction H orthogonal to the transverse direction Q. In the hinge area the two conductors 31, 32 can at least extend in sections in an aligned manner with view in transverse direction Q or otherwise have extensions that distinguish from each other.

As schematically illustrated in FIG. 4, the first conductor 31 can be electrically connected with the core 33 at a connection location 40 in the area of the support cavity 25, e.g. by welding, soldering or gluing. The electric connection between the first connection location 40 and the first tissue contact surface 17 is created by the electrically conductive core 33 of the first branch 11 or the first jaw 14. As an alternative to this embodiment, the first conductor 31 could also extend continuously to the first tissue contact surface 17. In a further embodiment the connection location 40 and the first handling part 19 could also be arranged farther away from the support cavity 25. This is dependent from how far an electrically conductive core 33 extends in the first branch 11 from the first jaw 14 in direction toward the proximal end or the electric connection device 29.

The first conductor 31 and the second conductor 32 each have a connection section 41 that can have a substantially rectangular contour. Alternatively to this the connection section 41 can also have a round and particularly circular cross-section. The connection section 41 is at least partly accessible from outside the first branch 11 and serves to create the electric connection with the electric connection device 29. The connection sections 41 can be part of the electric connection device 29.

A conductor section 42 adjoins the electric connection section 41 in the first conductor 31, as well as in the second conductor 32, wherein the conductor section 42 has the shape of a strip conductor. The conductor section 42 has a rectangular cross-section. In transverse direction Q the thickness of the conductor section 42 is less than the width in height direction H thereof.

As already explained, the conductor section 42 of the first conductor 31 can be electrically connected with the core 33 of the first branch 11 at the connection location 40. The conductor section 42 of the second conductor 32 has a contact section 44 at its distal end 43 that is the end opposite its connection section 41. The contact section 44 comprises at least one and according to the example, multiple contact parts 45. The contact section 44 with the at least one contact part 45 is configured to establish an electric connection with an electrically conductive area of the support pin 24. For this the at least one contact part 45 is in contact with an outer surface and according to the example, a circumferential surface 46 of the electrically conductive area of the support pin 24. In the embodiment the support pin 24 is part of an electrically conductive core 33 of the second branch 12 and thus electrically conductive as a whole. The support pin 24 is at least partly free from the electrically insulating outer layer 34 at its circumferential surface, such that an electric connection with the at least one contact part 45 of the contact section 44 can be established.

An embodiment of the contact section 44 is illustrated in FIGS. 10 and 11. In this embodiment the contact section 44 completely surrounds the support pin 24 in a circumferential direction about the pivot axis S. The contact parts 45 are according to the example arranged with distance to each other in circumferential direction about the pivot axis S and particularly regularly distributed. As an alternative to this embodiment, the contact section 44 can only partly surround the support pin 24 in circumferential direction about the pivot axis S, preferably about at least 50% or at least 60% or at least 70% of the circumference. Thus, the contact section 44 can be fork-like configured as an alternative to the illustrated embodiments.

Figure 12:
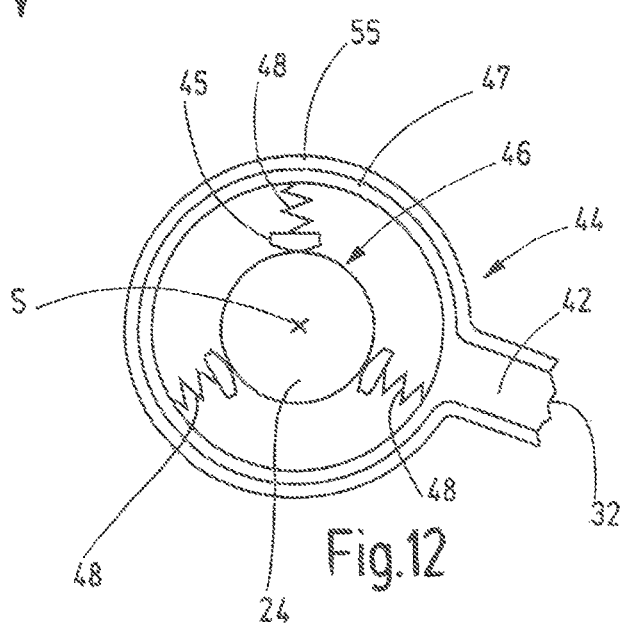
Figure 13:
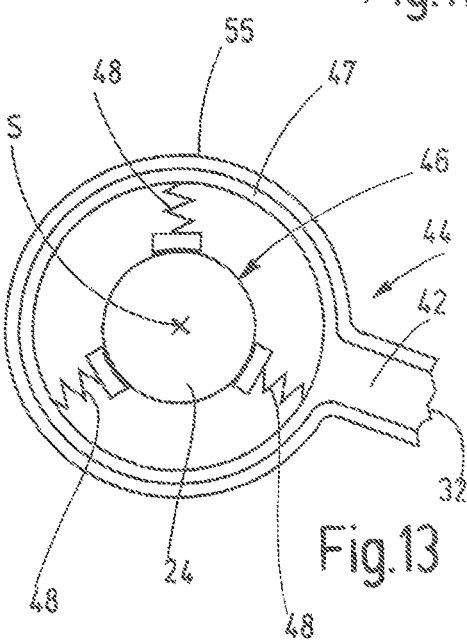

The principle of electric contacting between the circumferential surface 46 of the support pin 24 and the at least one contact part 45 is illustrated in FIGS. 12 and 13. Each contact part 45 can be in a substantially line-shaped contact with the circumferential surface 46 of the support pin 24 parallel to the pivot axis S, as exemplarily shown in FIG. 12. Such a line-shaped contact is created, particularly if a contact part 45 comprises a curvature on the side facing the circumferential surface 46 that does not correspond to the curvature of the circumferential surface 46 and can be configured in a convex or planar manner. As an alternative to this, each contact part 45 can comprise a concave curvature on its side facing the circumferential surface 46 that corresponds with the curvature of the circumferential surface 46 in circumferential direction about the pivot axis S, such that a substantially two-dimensional contact is created between the contact part 45 and the circumferential surface 46 (FIG. 13).

As in addition shown in FIGS. 12 and 13 in a block-diagram-like schematic manner, the at least one contact part 45 is urged radially toward the pivot axis S against the circumferential surface 46 of the support pin 24. This can be achieved, for example by an elastic deformation of at least a part of the contact section 44. Separate biasing means for radially biasing of the at least one contact part 45 against the support pin 24 are not provided according to the example, but the radial biasing force is created by the contact section 44 itself.

For this the contact section 44 comprises at least one support part 47 that is supported indirectly or directly at the first branch 11 or at a wall of the first branch 11 that borders the opening 38. The support part 47 can extend ring-shaped about the pivot axis S, as illustrated in FIGS. 10-13.

In the embodiment shown in FIGS. 10 and 11 the contact section 44 comprises additionally at least one holding part 48 at which one, multiple or all of the provided contact parts 45 are arranged. The holding part 48 is elastically biased in direction toward the support pin 24. The biasing is created by an elastic deformation of the holding part 48, if the at least one contact part 45 arranged at the holding part 48 abuts against the circumferential surface 46 of the support pin 24 and in so doing, is deflected away from the pivot axis S out of a rest position. The at least one contact part 45 takes the rest position in case the holding part 48 is not elastically deformed. Due to the deformation of the at least one holding part 48, it is achieved that the contact part or contact parts arranged thereon are pressed with a radial biasing force against the circumferential surface 46.

The holding parts 48 are schematically illustrated as springs in FIGS. 12 and 13. The constructive configuration of the holding parts 48 can vary.

In the embodiment illustrated in FIGS. 10 and 11 a through hole 49 is provided between the at least one support part 47 and each holding part 48 with view radial to the pivot axis S. The through hole 49 extends completely through the contact section 44 in transverse direction Q. According to the example, the through hole 49 has a circular arc-shaped form in circumferential direction about the pivot axis S. In the illustrated embodiment three holding parts 48 and three through holes 49 adjoining thereto are provided. The through holes 49 are arranged with distance to each other in circumferential direction about the pivot axis S. According to the example, the holding parts 48 each support one contact part 45 in their center area in circumferential direction about the pivot axis S. According to the example, the contact part 45 has a cylindrical contour. Each holding part 48 thus forms a kind of leaf spring, wherein the respective adjacent through holes 49 provide a radial clearance allowing an elastic deformation of the respective holding part 48.

Instead of a contact part 45 with a cylindrical contour, as shown in the basic illustration in FIG. 15, the contact part 45 with a different configuration can be arranged at each holding part 48. FIG. 16 shows an embodiment for a contact part 45 in which in circumferential direction about the pivot axis S two adjacent convex curved surface sections are provided that abut at the circumferential surface 46 of the support pin 24.

The contact part 45 in the embodiment according to FIG. 17 has a surface section in contact with the circumferential surface 46 of the support pin 24, the curvature of which corresponds substantially with the curvature of the circumferential surface 46.

Alternative embodiments for holding part 48 are illustrated in FIGS. 18 and 19. In these embodiments the holding part 48 is bent one time or multiple times and can have, e.g. an L-shaped (FIG. 18) or S-shaped (FIG. 19) configuration, such that a radial clearance 50 between the at least one contact part 45 and the support part 47 or multiple of such clearances 50 are created. Thus, the at least one contact part 45 is movably arranged in a spring-elastic manner radial to the pivot axis S.

A further configuration possibility for the contact section 44 is shown in FIG. 14. In this embodiment multiple support parts 47 are arranged with distance to each other in circumferential direction about the pivot axis S. Two directly adjacent support parts 47 are joined with each other by one web-shaped holding part 48. At least one contact part 45 is provided at the holding part 48 or formed by the holding part 48. In the embodiment the web-shaped holding parts 48 are arc-shaped curved toward the pivot axis S and abut the respective center area between the two adjacent support parts 47 at the circumferential surface 46 of the support pin 24 and form at this location the contact part 45.

Figure 20:
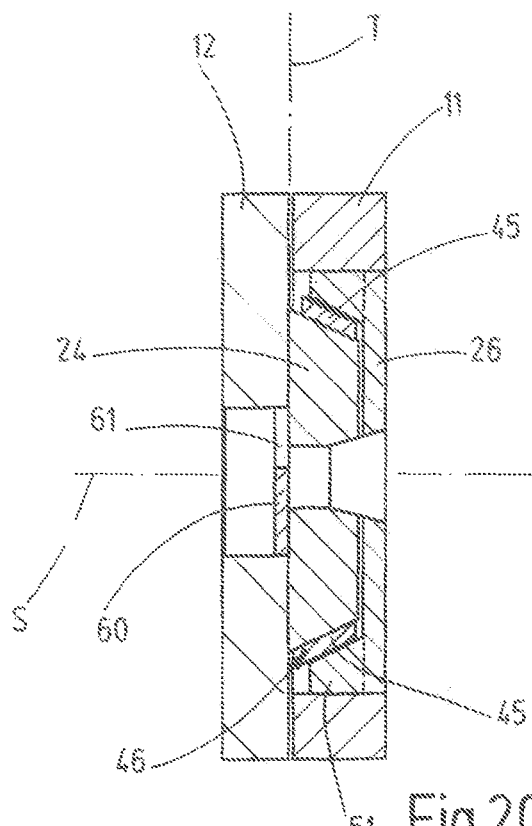
Figure 21:
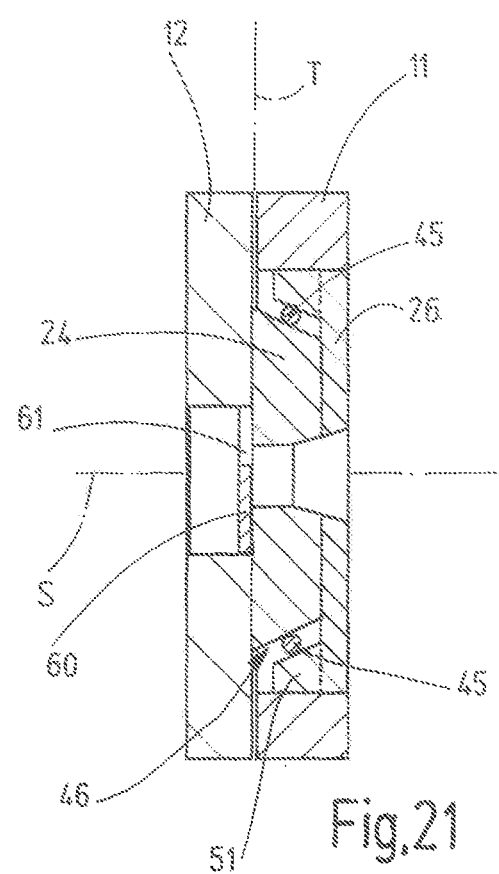
Figure 22:
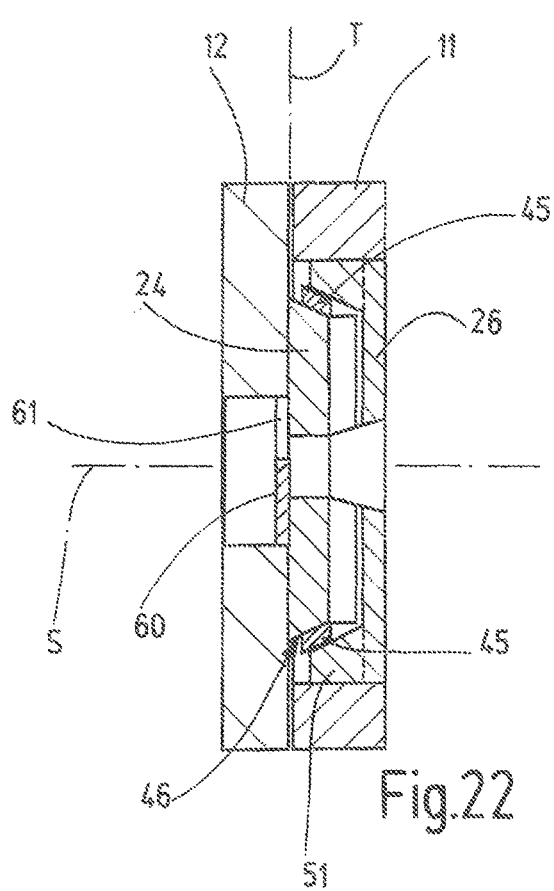

In the embodiments described so far the circumferential surface 46 of the support pin 24 is configured according to a cylinder skin surface coaxially to the pivot axis S. In FIGS. 20-23 alternative embodiments for the support pin 24 are schematically illustrated, wherein particularly the outer surface thereof comprises different contours and/or orientations for abutment with the contact part 45. The support pin 24 can be conically as a whole (FIGS. 20 and 21) or can at least comprise a conical section (FIG. 22). The conical shape is provided such that the support pin 24 tapers at least in sections toward the locking part 26. The area in which the at least one contact part 45 of the contact section 44 abuts is configured conically in these embodiments. The contact part 45 or the contact section 44 are illustrated in FIGS. 20 and 22 only highly schematically. As in the embodiments described so far, the contact part 45 or contact section 44 can have different configurations.

A pressing part 51 is provided at the locking part 26 in this configuration that presses the at least one contact part 45 axially in direction parallel to the pivot axis S against the circumferential surface 46 of the conical section of the support pin 24. The pressing part 51 can be arranged at the locking part 26 and forms an individual part that is supported at the locking part 26 or can be integrally formed with the locking part 26. Due to the axial force on the at least one contact part 45, also a radial force is created due to the circumferential surface of the support pin 24 extending obliquely to the pivot axis S, wherein the radial force urges the at least one contact part 45 against the circumferential surface 46. In this embodiment a holding part 48 in the contact section 44 that is elastically resiliently supported in radial direction can be omitted.

Figure 23:
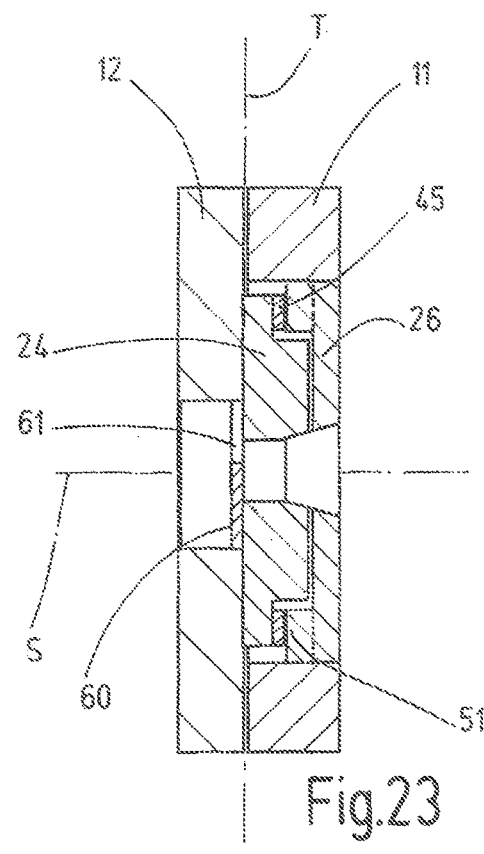

In the embodiment illustrated in FIG. 23 the outer surface of the support pin 24 comprises a ring surface 52 against which the at least one contact part 45 can abut. The ring surface 52 is orientated axially and extends according to the example in a plane that is orientated orthogonal to the pivot axis S. For example, the ring surface 52 can be formed by a step of the support pin 24 that forms a transition location between sections of the support pin 24 that adjoin each other. The section with the larger diameter of the support pin 24 adjoins the second branch 12. A pressing part 51 can be provided at the locking part 26 also in this embodiment that presses the at least one contact part 45 axially in direction parallel to the pivot axis S against the ring surface 52 of the support pin 24.

As explained above, the first conductor 31 and the second conductor 32 extend in an opening 38 of the second branch 12. In order to avoid electric contacting of the two conductors 31, 32 with each other, an electrically insulating intermediate layer 55 is arranged between the two conductors 31, 32 in this embodiment (FIG. 2). The electrically insulating intermediate layer 55 can be preferably fixedly connected with one of the conductors and according to the example, with the second conductor 32. For example, it can be connected on the second conductor 32 by creating a form fit connection and/or an adhesive connection. In an embodiment the intermediate layer 55 can be form fit connected or overmolded on the second conductor 32 or can be connected with the second conductor 32 by injection molding.

The intermediate layer 55 at the second conductor 32 serves, according to the example, also to ensure an electrical insulation between the second conductor 32 and the electrically conductive core 33 of the first branch 11. The intermediate layer 55 can enclose the second conductor 32 at one or more sides, as schematically illustrated in FIG. 10. For example, the at least one support part 47 can be supported by means of the intermediate layer 55 in the opening 38 at the first branch 11.

The electrosurgical instrument 10, according to the embodiments described above, can be manufactured as follows:

The two conductors 31, 32 are separated from one plate 39 or from different plates 39, e.g. by stamping, laser beam cutting, water jet cutting, etching or the like. Preferably an electrically insulating intermediate layer 55 is then applied on the second conductor 32, e.g. by inserting the second conductor 32 in a die and overmolding the second conductor 32 at least partly with the electrically insulating intermediate layer 55.

Subsequently the two conductors 31, 32 that are separated by the intermediate layer 55 are commonly placed in a first die together with an electrode that comprises the first tissue contact surface. By inserting of pourable, curable material in the first die and subsequent curing, the first branch 11 is created that comprises the first tissue contact surface 17 and the two conductors 31, 32. The first branch 11 is manufactured in the first form such that a support cavity 25 is created.

An electrically conductive support pin 24 and an electrically conductive electrode with the second tissue contact surface 18 is arranged in a second die, in which pourable, curable material is inserted. A second branch 12 is created by curing the material. After the manufacturing of the two branches 11, 12 they are joined with each other in a hinged manner by inserting the support pin 24 in the support cavity 25. During the creation of the hinged joint, the at least one contact part 45 of the contact section 44 gets into contact with the circumferential surface of the electrically conductive support pin 24, such that an electrically conductive contact between the second conductor 32 with the support pin 24 and via the support pin 24 with the second tissue contact surface 18 is established.

In the preferred embodiment the electrosurgical instrument 10 only has one single hinge 13 with one single support pin 24 and one single support cavity 25 into which the support pin 24 extends.

The support cavity 25 opens in a first abutment surface 56 on a side opposite the locking part 26. The first abutment surface 56 extends in a plane orthogonal to the pivot axis S. The first abutment surface 56 can be provided at the outer side of an area of the electrically insulating outer layer 34 that surrounds the core 33 of the first branch 11 (FIG. 8).

A second abutment surface 57 is provided at the second branch 12 from which the support pin 24 extends to its free end 24a. The second abutment surface 57 extends preferably in a plane orthogonal to the pivot axis S. The second abutment surface 57 can be formed by the outer side of an area of the electrically insulating outer layer 34 around the core 33 of the second branch 12 (FIG. 8).

The first abutment surface 56 and/or the second abutment surface 57 form a separation plane T and according to the example, a planar separation plane (FIG. 7). The two abutment surfaces 56, 57 abut at each other or face each other and are arranged adjacent to each other. Preferably, the two abutment surfaces 56, 57 abut directly against each other. In a modified embodiment a sliding ring or the like can be alternatively arranged between the two abutment surfaces 56, 57.

The hinge 13 formed by the support pin 24 and the support cavity 25 is arranged with view in transverse direction Q only on one side of the preferably planar separation plane T. No hinge or hinge location is present on the respective other side.

The separation plane T formed by the second abutment surface 57 is not penetrated by the first branch 11 in the circumferential area about the hinge 13. The separation plane T in this case also forms a limitation plane in the hinge area of hinge 13 through which the first branch 11 does not extend.

An embodiment of the electrosurgical instrument 10 comprises a knife 60 that is movably supported in a guided manner in a movement direction B orthogonal to the transverse direction Q. The movement direction B extends parallel to the extension direction of the second branch 12. The movement direction B can extend at least partly curved depending on the configuration of the jaws 14, 15.

For guiding the knife 60 a knife guide cavity 61 is present in the second branch 12 that comprises a rectangular cross-section according to the example. The knife 60 can be supported on the side at the walls of the knife guide cavity 61. The knife guide cavity 61 has a guide section 62 that extends in movement direction B in the hinge area of hinge 13 and thus in the area of the support pin 24. Along this guide section 62 the second branch 12 is provided with a transverse cavity 63 that extends in transverse direction Q and is penetrated by the pivot axis S. The transverse cavity 63 opens at one end in the guide section 62 of the knife guide cavity 61 and opens at the respective other end in transverse direction Q in an outer side 64 of the second branch 12. According to the example, this outer side 64 faces away from the first branch 11.

In the embodiment the transverse cavity 63 is configured as a slot hole 65 extending in movement direction B. The length of the transverse cavity 63 or the slot hole 65 in movement direction B along the guide section 62 of the knife guide cavity 61 is at least as long and according to the example, longer than the outer diameter of the support pin 24. Through the transverse cavity 63 the accessibility to the knife guide cavity 61 is guaranteed that is limited on the other side in transverse direction Q at least partly by an axial end face 24b of the support pin 24. In the embodiment the axial end face 24b adjoins directly to the guide section 62 of the knife guide cavity 61.

The support pin 24 extends in transverse direction Q from the axial end face 24b to the free end 24a. Orthogonal to the pivot axis S the support pin 24 is configured without through openings according to the example. At least the support pin 24 has no through opening that is aligned with the knife guide cavity 61 between its axial end face 24b and its free end 24a. Rather it is offset in transverse direction Q from the knife guide cavity 61.

With view in movement direction B the knife guide cavity 61 is open on both sides of the axial end face 24b of the support pin 24 to the second abutment surface 57 and thus also to the first abutment surface 56. If the branches 11, 12 are closed in case the jaws 14, 15 abut at each other in the area of the tissue contact surfaces 17, 18, the knife guide cavity 61 is limited in movement direction B adjacent to the axial end face 24b of the support pin 24 by the first abutment surface 56.

As particularly apparent from FIG. 7, the axial end face 24b of the support pin 24 extends according to the example in the same plane as the second abutment surface 57. The axial end face 24b could also be arranged offset with reference to the second abutment surface 57. In each case the knife guide cavity 61 is limited in the area, in which it adjoins the axial end face 24b of the support pin 24 on at most three sides by the support pin 24.

Because of the extension of the knife guide cavity 61 through the pivot axis S, an eccentric arrangement of the knife 60 is avoided. Thus, the knife 60 does not execute an eccentric movement about the pivot axis S also during a pivot movement of the branches 11, 12 relative to each other. Because the hinge 13 is arranged only on one side with reference to the knife guide cavity 61, a simply and cheaply producible configuration of the electrosurgical instrument 10 is achieved that allows a good accessibility to the cavities and thus also an advantageous cleaning or sterilization.

In a preferred embodiment in addition a purge opening 70 is provided in the first branch 11 that extends substantially orthogonal to the pivot axis S. The purge opening 70 opens at one end in the support cavity 25 and on the respective opposite end in an outer side 71 of the first branch 11. The purge opening 70 is arranged offset to the pivot axis S in height direction H. It extends substantially radially to the pivot axis S.

Figure 9:
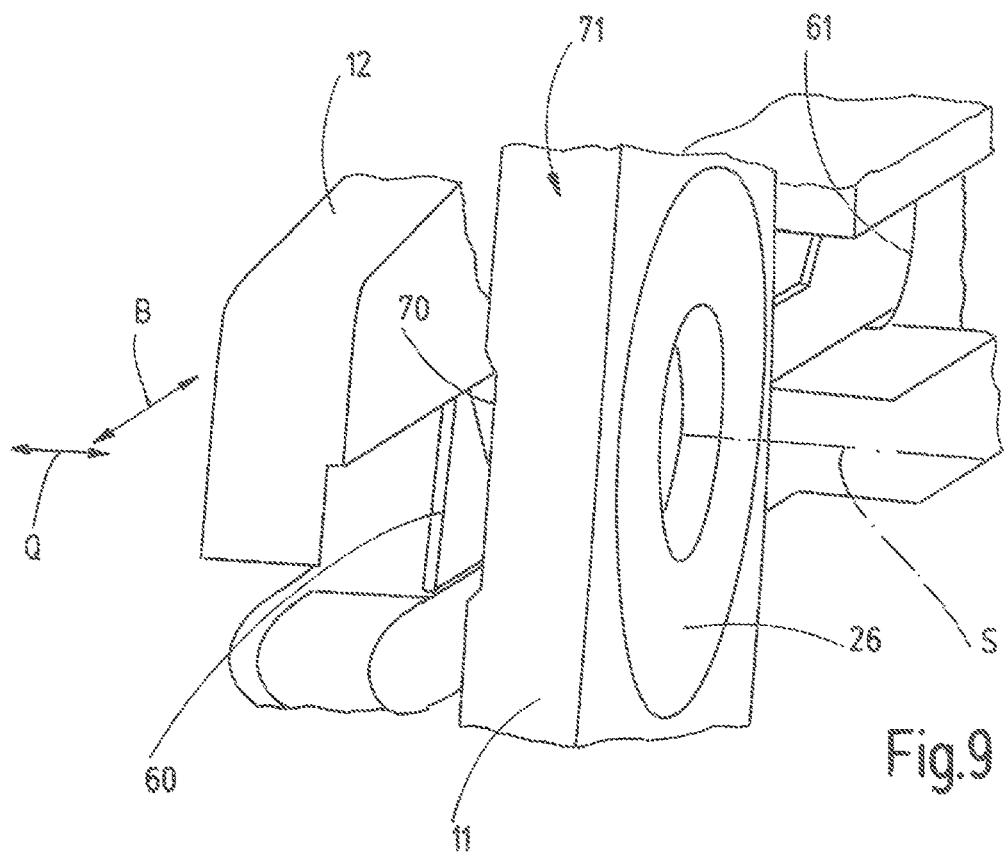
FIG. 9 shows a schematic perspective partial illustration of the two branches of the electrosurgical instrument in an opened position of the branches.

During a pivot movement of the two branches 11, 12 relative to each other, the purge opening 70 executes a pivot movement about the pivot axis S. In a predefined opened position, if the two tissue contact surfaces 17, 18 are arranged with distance to each other, the extension direction of the purge opening 70 is orientated parallel to movement direction B of the knife 60 and the purge opening 70 extends along a section of the knife guide cavity 61 as schematically illustrated in FIG. 9. In doing so, access to the knife guide cavity 61 and the knife 60 arranged therein in a guided manner is improved, particularly with regard to the cleaning of the instrument 10 after its use.

The embodiments of the electrosurgical instrument 10 described above can be combined with each other or can be independently realized from each other. Particularly the arrangement of the knife guide cavity 61 guiding the knife 60 offset to the side of the hinge 13 can be realized independently from the configuration of electric contacting of the tissue contact surfaces 17, 18 via the two conductors 31, 32. These aspects can be realized separately from each other.

The invention refers to an electrosurgical instrument 10 with first branch 11 and second branch 12. The two branches are pivotably arranged at each other by means of a hinge 13. The hinge 13 is formed by a support pin 24 at the second branch 12 and a corresponding support cavity 25 at the first branch 11. Preferably one single hinge 13 with one single support cavity 25 and one single support pin 24 is provided. At one side adjacent to the hinge location at which the support pin 24 extends into the support cavity 25, a knife guide cavity 61 is provided in the second branch 12 for a moveable guided support of a knife 60. Parallel to the pivot axis defined by the hinge 13, the knife guide cavity 61 is arranged adjacent and preferably directly adjoining to an axial end of the support pin. The hinge 13 or the hinge location formed by the hinge at which the support pin 24 is arranged in the support cavity 25 is only arranged on one side of the knife guide cavity with view in a direction parallel to the pivot axis. The respective other side is free from hinge components and does not contain means used for pivotably supporting the two branches at each other along the pivot axis.

LIST OF REFERENCE SIGNS 10 electrosurgical instrument
11 first branch
12 second branch
13 hinge
14 first jaw
15 second jaw
16 handling unit
17 first tissue contact surface
18 second tissue contact surface
19 first handling part
20 second handling part
24 support pin
24a free end of the support pin
24b axial end face of support pin
25 support cavity
26 locking part
27 depression
28 ring shoulder
29 electric connection device
30 external electric connection
31 first conductor
32 second conductor
33 core
34 outer layer
38 opening
39 plate
40 connection location
41 connection section
42 conductor section
43 distal end of the second conductor
44 contact section
45 contact part
46 circumferential surface
47 support part
48 holding part
49 through hole
50 clearance
51 pressing part
52 ring surface
55 intermediate layer
56 first abutment surface
57 second abutment surface
60 knife
62 knife guide cavity
62 guide section
63 transverse cavity
64 outer surface of the second branch
65 slot hole
70 purge opening
71 outer surface of the first branch
B movement direction
Q transverse direction
S pivot axis
T separation plane

The invention claimed is:

1. An electrosurgical instrument (10), comprising:
a first branch (11) that comprises a support cavity (25) and a second branch (12) that comprises a support pin (24) that extends in the support cavity (25) of the first branch (11), thus forming a hinge (13) by means of which the first branch (11) is pivotably arranged about a pivot axis (S) at the second branch (12),
a knife guide cavity (61) provided in the second branch (12) in which a knife (60) is moveably supported in a movement direction (B) in a guided manner, wherein the support pin (24) is arranged on one side of the knife guide cavity (61) in a transverse direction (Q) parallel to the pivot axis (S) and wherein the second branch (12) is configured without an additional support pin and without an additional support cavity on an opposite side of the knife guide cavity (61) in the transverse direction (Q), wherein the support pin (24) has an axial end surface (24*b*) that directly adjoins the knife guide cavity (61), wherein the support pin (24) is configured without a through-opening that allows the knife (60) to pass therethrough, and wherein the support pin (24) is configured without a through-opening that extends through the support pin (24) transverse to the pivot axis between the axial end surface (24*b*) and an opposite axial end surface (24*a*) thereof.

2. The electrosurgical instrument according to claim 1, wherein the pivot axis (S) extends through the knife guide cavity (61).

3. The electrosurgical instrument according to claim 1, wherein the first and second branches comprise no additional support pins or support cavities.

4. The electrosurgical instrument according to claim 1, wherein the first branch (11) has a first abutment surface (56) in which the support cavity (25) opens, and the second branch (12) has a second abutment surface (57) from which the support pin (24) extends, and wherein the first and second abutment surfaces (56, 57) abut against each other.

5. The electrosurgical instrument according to claim 4, wherein the knife guide cavity (61) is open to the second abutment surface (57).

6. The electrosurgical instrument according to claim 5, wherein the knife guide cavity (61) is open to the second abutment surface (57) on either side of the support pin (24) with respect to the movement direction (B).

7. The electrosurgical instrument according to claim 4, wherein the first abutment surface (56), the second abutment surface (57), or both the first and second abutment surfaces (56, 57) form a separation plane, wherein the first and second branches (11, 12) are hinged at each other only by the hinge (13) arranged on one side of the separation plane (T).

8. The electrosurgical instrument according to claim 7, wherein the knife guide cavity (61) directly adjoins or is spaced from the separation plane (T).

9. The electrosurgical instrument according to claim 1, further comprising a transverse cavity (63) in the second branch (12) that extends in the transverse direction (Q) and opens in the knife guide cavity (61) at an end thereof and opens in an outer side (64) of the second branch (12) at an other end.

10. The electrosurgical instrument according to claim 9, wherein the transverse cavity (63) is configured as slot hole (65) having a length in movement direction (B) that is at least as long as a diameter of the support pin (24).

11. The electrosurgical instrument according to claim 1, wherein an area of the support pin (24) adjoining the knife guide cavity (61) delimits the knife guide cavity (61) at at most three sides.

12. The electrosurgical instrument according to claim 1, further comprising a purge opening (70) in the first branch (11) that opens in the support cavity (25) at one end of the purge opening and opens at an outer side (71) of the first branch (11) at another end of the purge opening.

13. The electrosurgical instrument according to claim 12, wherein the purge opening (70) is open on a side facing the second branch (12).

14. The electrosurgical instrument according to claim 13, wherein the purge opening (70) extends between its two ends along a section of the knife guide cavity (61) in an opened position of the first and second branches (11, 12).

15. An electrosurgical instrument (10), comprising:
a first branch (11) that comprises a support cavity (25) and a second branch (12) that comprises a support pin (24) that extends in the support cavity (25) of the first branch (11), thus forming a hinge (13) allowing the first branch (11) to be pivotably arranged about a pivot axis (S) at the second branch (12), a knife guide cavity (61) provided in the second branch (12) in which a knife (60) is moveably supported in a movement direction (B) in a guided manner, wherein the support pin (24) is arranged on one side of the knife guide cavity (61) in a transverse direction (Q) parallel to the pivot axis (S) and wherein the second branch (12) is configured without an additional support pin and without an additional support cavity on an opposite side of the knife guide cavity (61) in the transverse direction (Q), and a transverse cavity (63) in the second branch (12) that extends in the transverse direction (Q) and opens in the knife guide cavity (61) at an end thereof and opens in an outer side (64) of the second branch (12) at an other end.

* * * * *